United States Patent [19]

Demsky et al.

[11] 4,033,698
[45] July 5, 1977

[54] APPARATUS FOR TEXTILE COLOR ANALYSIS

[75] Inventors: Herbert M. Demsky, Wappingers Falls; Einar S. Mathisen, Poughkeepsie; Paul A. Schumann, Jr., Wappingers Falls; Alvin H. Tong, Poughkeepsie, all of N.Y.

[73] Assignee: International Business Machines Corporation, Armonk, N.Y.

[22] Filed: Oct. 10, 1975

[21] Appl. No.: 621,335

[52] U.S. Cl. .............................. 356/173; 250/227; 356/210

[51] Int. Cl.² ........................................... G01J 3/46

[58] Field of Search .......... 250/227, 226; 356/173, 356/176, 177, 186, 188, 189, 199, 209, 210

[56] References Cited

UNITED STATES PATENTS

| 1,988,556 | 1/1935 | Hunter | 356/210 |
|---|---|---|---|
| 3,455,637 | 7/1969 | Howard | 250/227 |
| 3,476,482 | 11/1969 | Howard et al. | 250/227 |
| 3,549,264 | 12/1970 | Christie | 250/227 X |
| 3,806,256 | 4/1974 | Ishak | 356/186 |
| 3,885,878 | 5/1975 | Ishak | 356/188 X |
| 3,935,436 | 1/1976 | Holschlag et al. | 356/177 X |

Primary Examiner—F. L. Evans
Attorney, Agent, or Firm—D. R. McKechnie

[57] ABSTRACT

In a textile color analyzer, a sample of textile is supported on the pad of an elevator mechanism that holds the sample against an instrument head. The head has an opaque housing provided with a chamber having an opening therein. A glass plate is mounted in the head and covers the opening and presses against the textile sample to provide a stable reference plane. The head includes an illuminating fiber optic bundle that directs light substantially perpendicular to the textile sample. A plurality of additional fiber optic bundles are mounted to receive diffuse light reflected from the sample. The elevator includes a pad of translucent polyethylene material that backs up the textile sample and takes on the color of the sample so that there are no adverse effects due to light showing through the sample and reflecting from the plate.

5 Claims, 6 Drawing Figures

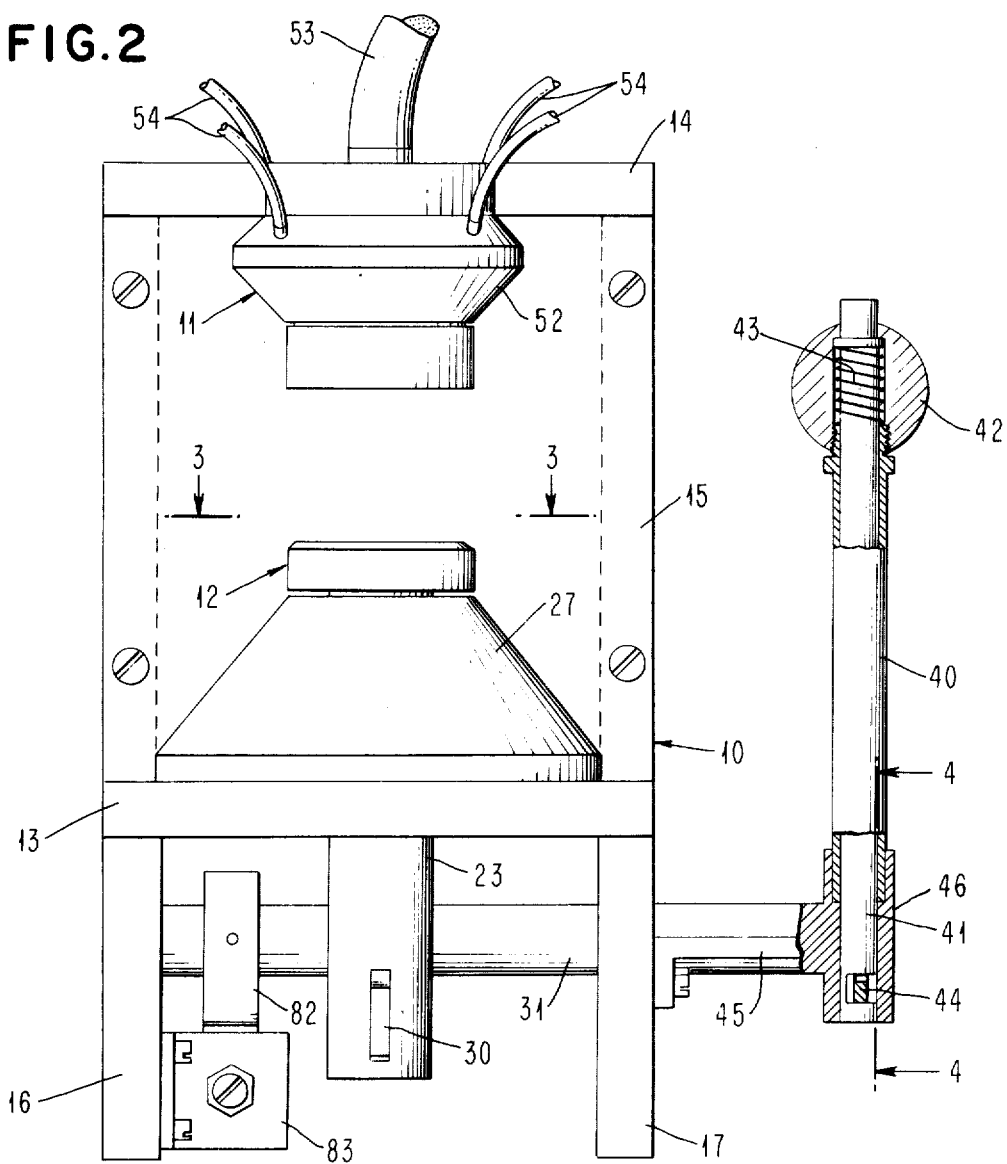
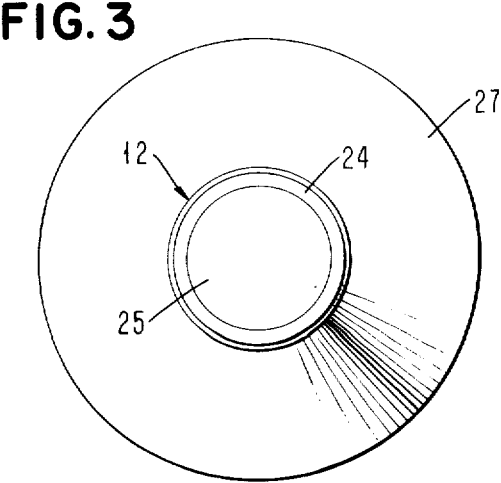
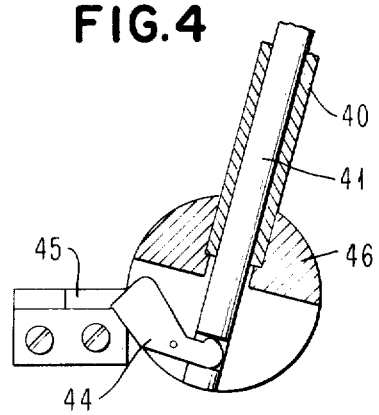

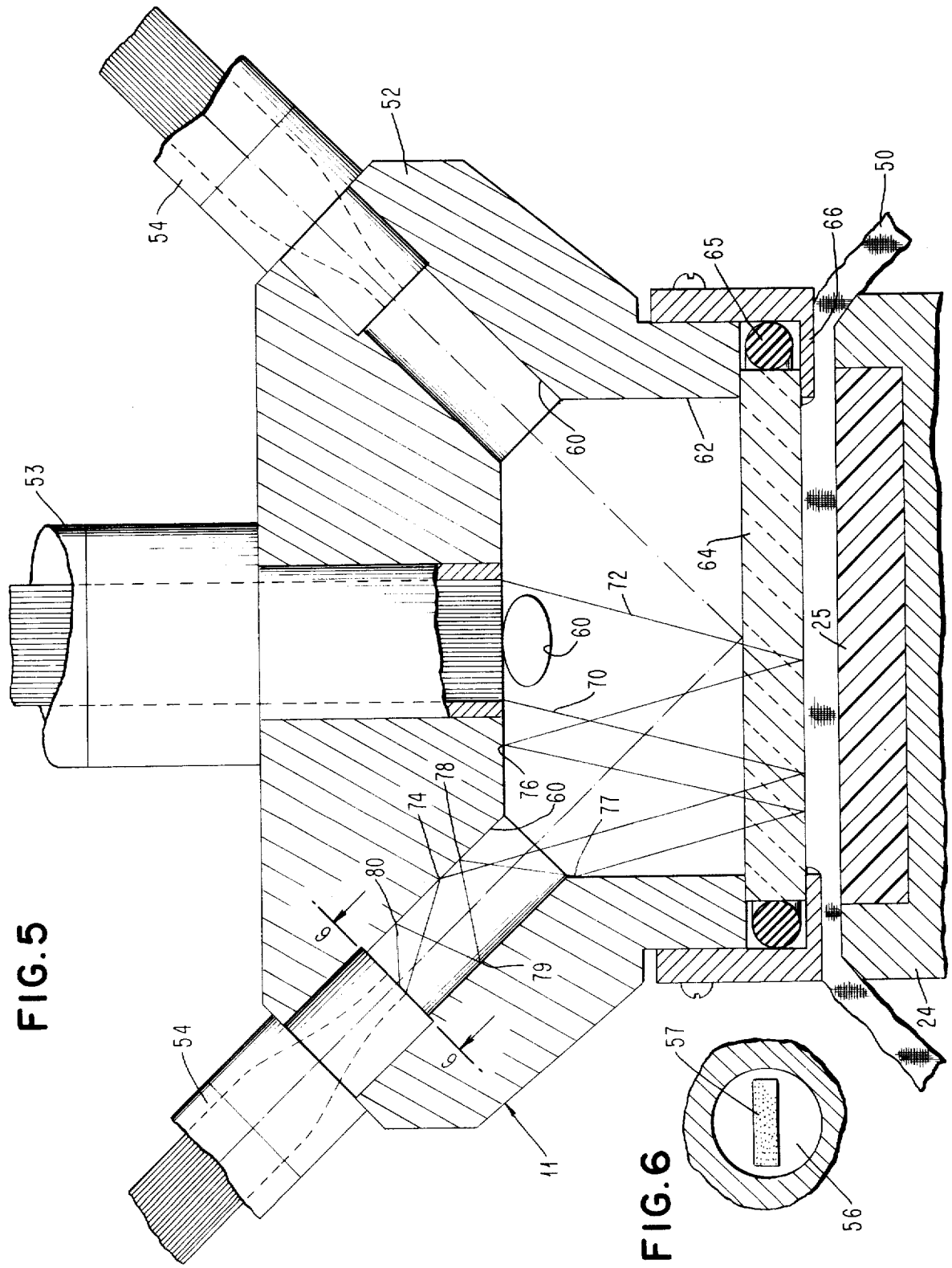

APPARATUS FOR TEXTILE COLOR ANALYSIS

RELATED PATENT APPLICATIONS

Filed concurrently herewith are the following applications both of which are assigned to the assignee of the present application:

Application A - "Textile Color Analyzer Calibration" by P. A. Schumann et al, Ser. No. 621,334, Filed Oct. 10, 1975, is directed to the calibration technique for a spectrophotometer in which the apparatus of the present invention is used.

Application B - "Apparatus for Textile Color Analysis", by H. M. Demsky et al, Ser. No. 621,333, Filed Oct. 10, 1975, now U.S. Pat. No. 3,999,860, is directed to apparatus having a polyethylene pad that backs up the textile sample while it is being held during measurement. Such a pad is included in the combination of the present invention.

FIELD OF THE INVENTION

This invention relates to apparatus for measuring or analyzing the color of objects or of materials such as textiles. More particularly, it relates to novel apparatus for illuminating a textile sample while it is held in a fixed position, and for receiving or collecting diffuse light reflected from the sample.

PRIOR ART

Various instruments are known for measuring the reflectance of textile samples in order to analyze the color characteristics of such samples. In general, such instruments are of two types. One type measures the tristimulus values directly and the other type analyzes the color by use of a spectrophotometer that measures the reflectance at different wavelengths across the spectrum of visible light. The test sample is illuminated and the light reflected from the sample is detected. Since the total light reflected includes both specular and diffuse components, and since the specular component gives rise to erroneous analysis, it is common to separate these components in various different ways. The diffuse component is used to measure the true color characteristics of the sample. The present invention is directed to a system which collects primarily the diffuse component of the reflected light.

As is known in the prior art, color measurements on textiles presents problems due to the thinness thereof. With thin samples, light can pass through the sample and reflect from any backing plate backwardly through the sample with the result that the light collected for detection includes spectral components that are due to the backing plate. This plate is necessary to block out any stray light. To minimize this problem, the prior art techniques include using multiple layers of thin samples and the use of black or white backup plates. For such plates, some form of compensation or correction of any measurement is needed.

SUMMARY OF THE INVENTION

One of the objects of the invention is to provide novel apparatus for holding a sample while it is illuminated and while diffuse light reflected from the sample is collected.

Another object is to provide a sample holder in which the sample is held under force or pressure against a surface of a glass plate to establish a reference plane from which diffuse light is reflected from the sample.

Still another object is to provide a highly accurate spectrophotometer measuring head particularly adapted for analyzing the color of textiles.

A further object is to provide a head useful in analyzing the colors of textiles in which light is conducted to and away from the head by fiber optic bundles.

A still further object is to provide a novel head in which the light collection elements are disposed out of the primary path of any specular light ray reflected from the sample.

Another object is to provide a textile color measuring head useful for measuring thin samples of textiles.

Still another object is to provide a measuring head which avoids any problem due to light passing through the sample and reflecting from a backing plate.

Briefly, the invention generally comprises an opaque head having a first bore therein which receives the end of a fiber optic bundle that transmits light for illuminating the test sample. The head includes a chamber which opens towards one side of the head and the opening is covered by a glass plate coated with a non-reflective material to reduce surface reflectance. A manually actuated elevator mechanism is used to raise a test sample into contact with the head, the elevator mechanism including a pad of translucent material that takes on the color of the textile sample while it is being illuminated. The pad presses the sample against the outer surface of the glass plate. A plurality of additional fiber optic bundles have their ends mounted or connected to the head assembly for receiving light reflected from the sample and transmitting it to a spectrophotometer or other form of light analyzer. The receiving ends of these bundles are located outside of the direct path of any light ray specularly reflected from the object so as to receive primarily diffuse reflected light. The interior of the chamber is blackened to minimize internal reflections. Other objects and advantages of the invention will be apparent from the following detailed description of a preferred embodiment of the invention, taken in connection with the accompanying drawings wherein:

FIG. 2 is a front elevational view partly in section and with portions removed, of the apparatus of FIG. 1;

FIG. 3 is a top plan view looking along reference lines 3—3 of FIG. 2;

FIG. 4 is a side elevational detail view of the detent mechanism looking along reference lines 4—4 of FIG. 2;

FIG. 5 is an enlarged cross-sectional view through the head and support pad when a textile sample is held therebetween; and FIG. 6 is a detail view looking along reference lines 6—6 of FIG. 5.

Figure 1:
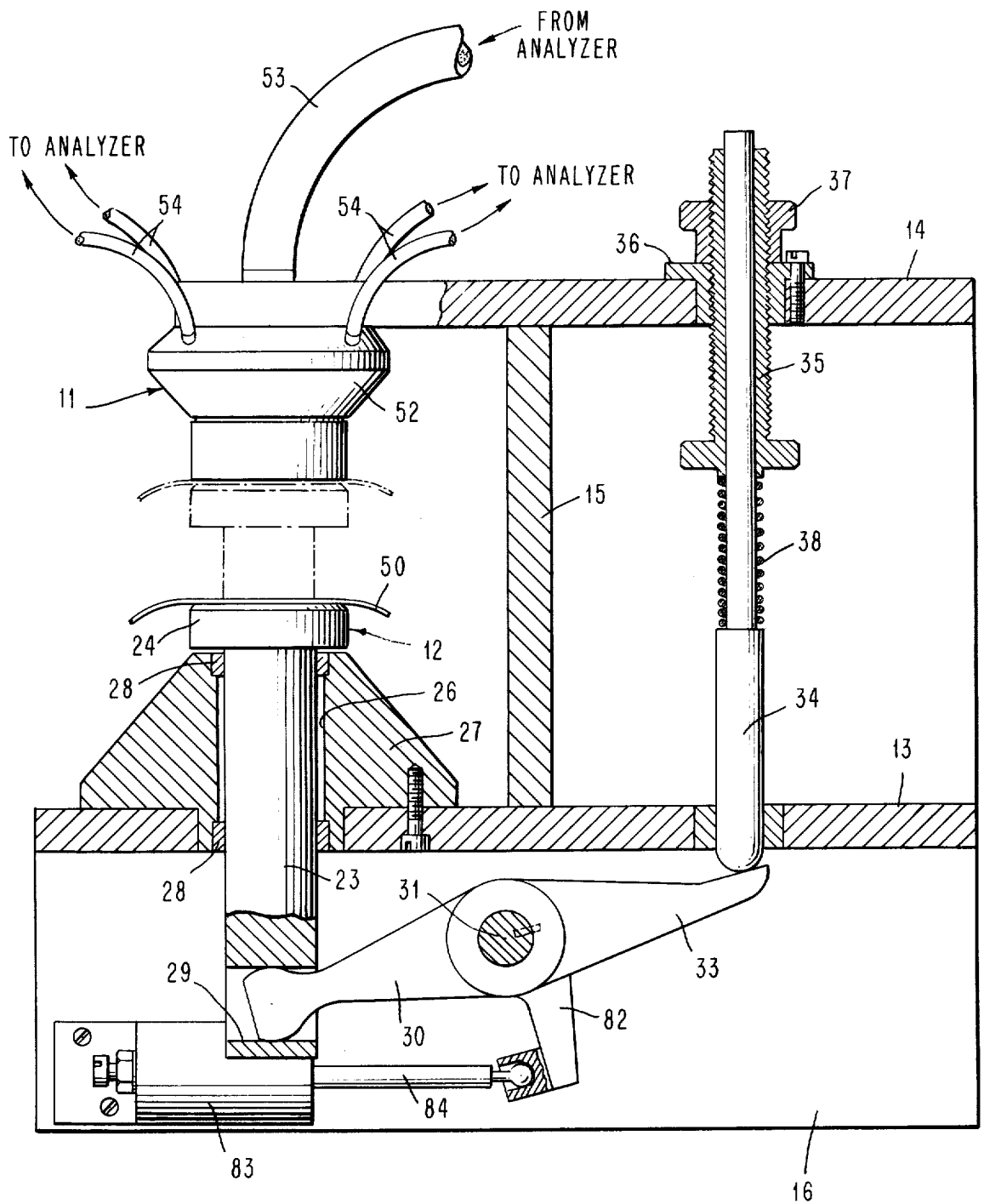
FIG. 1 is a side elevational view, partly in section and with portions removed, of a preferred embodiment of the invention.

Referring now to the drawings, and first to FIGS. 1 and 2, the invention comprises a metal base 10 having a head 11 mounted thereon in a fixed position over an elevator sample support 12. Base 10 comprises a plurality of plates 13 - 17 connected together in a conventional fashion such as by welding or by the use of threaded fasteners. Plate 13 is horizontal and underlies plate 14 on the front of which head 11 is mounted, plates 13 and 14 being connected to a vertical plate 15 extending therebetween. Plates 16 and 17 run along the bottom side of plate 13 and are adapted to rest upon a support surface, such as a tabletop connected with the instrument, in a position so that the operator has convenient access to placing a sample between head 11 and support 12.

Support 12 includes a vertical, cylindrical shaft 23 the upper end 24 of which is enlarged and has a pad 25 embedded therein, the upper face of 24 and 25 being flat and horizontal. Shaft 23 passes through a cylindrical bore 26 formed in a conical member 27 mounted on plate 13 beneath head 11. Bearings 28 guide shaft 23 for vertical movement between the full line and dotted line positions shown in FIG. 1. The lower end of shaft 23 has a slot 29 that receives one end of a radial arm 30 keyed to a shaft 31 for rotation therewith.

Shaft 31 extends through and is supported by plates 16 and 17 and has an enlarged end 46 connected to a handle 40. A detent actuating rod 41 extends vertically through handle 40 and through a knob 42 screwed on the upper end of handle 40. The upper end of actuating rod 41 projects above knob 42 and is adapted to be manually pressed for actuating the detent mechanism in the manner described below. A compression spring 43 mounted in knob 42 biases rod 41 upwardly so that the upper tip is exposed. The lower end of rod 41 is slotted and is connected to a bell crank type detent 44 that is engagable with a detent bar 45 mounted on plate 17 adjacent thereto.

A second radial arm 33 extends rearwardly from shaft 31 in alignment with arm 30 and abuts the lower end of a vertical pin 34. The lower part of pin 34 slidably passes through plate 13 and the upper end of pin 34 is of reduced diameter and passes through a threaded member 35 that is mounted in a threaded member 36 fixedly connected to plate 14. Member 35 is rotatable relative to member 36 whereby member 35 can be rotated and moved vertically to adjust the compressive force of a compression spring 38 mounted between the lower end of member 35 and a shoulder on pin 34. A lock nut 37 is mounted on the upper end of member 35 and can be tightened against member 36 to secure the biasing assembly.

The purpose of detent 44 is to lock elevator support 12 in the down position shown in full lines in FIG. 1 wherein the lower face of 24 is slightly above the upper end of 27. In such a position, spring 38 biases shaft 31 in a direction that wedges detent 44 against bar 45 and prevents upward movement of support 12. The support can be raised by grasping handle 40, pulling back on it slightly and then pressing rod 41 downwardly. This action pivots detent 44 away from bar 45 and the handle can then be pushed forwardly or allowed to move due to spring 38, until detent 44 clears 45. Thereafter, rod 41 can be released and support 12 moved upwardly to the dotted line position shown in FIG. 1. The support is lowered by pulling back on handle 40 until detent 44 cams or slides over bar 45 and assumes a locking position in engagement therewith.

As seen in FIGS. 1 and 2, head 11 comprises a housing 52 connected to a first fiber optic bundle 53 that is adapted to have its other end (not shown) connected to an instrument such as a spectrophotometer to receive light therefrom for illuminating sample 50. Four additional fiber optic bundles 54 are connected to head 11 for the purpose of receiving diffuse light reflected from sample 50 and transmitting it to the instrument for analysis. Bundles 54 are spaced 90° apart around housing 52. FIG. 5 is a view taken diametrically through head 11 through two of bundles 54. Each of the fiber optic bundles is of a conventional construction and comprises fiber optic strands randomly oriented, the ends of the bundles being secured by standard ferrules having reduced diameter tip portions plugged into housing 52. The fibers at the lower ends of bundles 54 are formed into elongated rectangles or slats 57 that extend horizontally across the lower ends of bundles 54. The fibers at the lower end of bundle 53 are formed into a circle and provides illumination to the test sample 50.

The lower ends of bundles 54 terminate at the upper ends of bores 60 formed in housing 52 and extending at 45° angles relative to the axis of housing 52 and spaced 90° apart coincident with the spacing of bundles 54. Housing 52 has a downwardly opening cylindrical bore 62 which bores 60 open into. A circular glass plate 64 is mounted in the lower end of housing 62 by means of a ring 66 and an O-ring 65. Ring 66 is integral with housing 62 and may be separately formed and connected thereto by either screw means or welding. Ring 66 has an outer diameter corresponding to that of head 24. The diameter of pad 25 is slightly greater than the diameter of bore 62 so as to underlie and completely close or cover the lower end of such bore. Head 52 may be formed of aluminum and the interior surfaces thereof are anodized black and painted with black anti-reflection paint to reduce and minimize internal reflectance. Plate 64 is preferably made of a quartz glass having low absorbance across the range of wavelengths of visible light. The surfaces are flat and parallel and are coated with an anti-reflective material to reduce the reflectance of such surfaces.

The location of slots 57 at the lower ends of each bundle is important, the slots being placed so as to minimize the effect of any specular reflectance within head 11. To understand this, two light rays 70 and 72 are schematically shown in FIG. 5. Light, as it emerges from the lower ends of each fiber optic strand, normally spreads out through an angle that is dependent upon the indices of refraction of the core material of an individual strand and of the cladding. A typical angle may be in the order of 16°. Light ray 70 represents the extreme condition of a ray emitted by the left most fiber optic strand in bundle 53 which ray follows the left edge of the cone of light emerging from the strand. Light ray 70 passes downwardly through the interior of bore 62 and is refracted through plate 64. Light ray 70 is then reflected off the top surface of sample 50. This ray then passes upwardly through bore 62 and into bore 60 where it hits the wall thereof at 74. The ray is then reflected off of this wall and misses slot 57. Slot 57 is thus positioned or set back into bore 60 whereby there is no direct reflective route for any specular light ray coming from the fiber optic bundles and wherein any such direct ray has to be reflected from the walls of the interior of housing 52 more than once in order to hit the slot. By virtue of the low reflectance characteristics of the black interior of housing 52, any light component due to specular reflection that hits slot 57 has an extremely low value. At the other extreme, light ray 72 similarly passes down through the chamber formed by bore 62 and is refracted through glass plate 64. The light reflected from the top surface of test sample 50 then passes upwardly through the bore and hits the top surface of the inner chamber at 76 whereby it is reflected downwardly. The light passes downwardly, through glass plate 64 and then upwardly and hits the wall at 77. The light ray then passes into bore 60 and hits the wall at 78, 79, and 80. By this time it will be appreciated that this light ray has been reflected from the interior surface of housing 52 at five different spots and still has not reached slot 57. Light rays emerging from other fibers within bundle 53 can be similarly traced but none will hit slot 57 without first being reflected from the interior walls of housing 52 at least twice.

The force of spring 38 is used to control the force with which support 12 presses test sample 50 against head 11. The sample is compressed under the force of spring 38 so that the material abuts the lower surface of plate 64. This surface provides a reference plane from which the fiber optic bundles are located fixed distances and thus prevents any erroneous readings that might occur if plate 64 were not present and if the fabric, tufts or fibers of sample 50 were allowed to extend into the head in an uncontrolled manner. To prevent damage to glass plate 64, it is recessed slightly due to the thickness of ring 66 so that it does not directly abut the upper end of head 24 or pad 25. A radial arm 82 is attached to shaft 31 adjacent to plate 16 and a dashpot mechanism 83 is mounted on plate 16 in alignment with the end of arm 82 so that an actuating rod 84 of the dashpot abuts arm 82. The dashpot mechanism is operative to limit movement of support 12 towards head 11 in the event that handle 40 slips out of or is let go of by the operator so that the elevator moves upwardly due to the compressive forces of spring 38.

Pad 25 is preferably made of white or colorless polyethylene and has the desirable optical characteristics of being translucent and having an index of refraction substantially equal to the indices of refraction normally encountered in textiles, such index being about 1.5. The matching indices minimizes any interface reflectance. Light that passes through the sample illuminates the polyethylene pad so that the pad takes on or appears to be of the same color as the sample and therefore light reflected from it has the same color characteristics as the sample. The pad does not absorb light from the sample and provides a high scattering of light reflected backwardly from it through the sample. The sample acts as though it is a transmission filter. The pad is effectively infinitely thick and satisfies the requirements of the well-known Kubelka-Munk theory for solving for layer reflectances. The actual pad thickness is one-sixteenth inch (1.6 mm) or greater and a pad of one-eighth inch is satisfactory. Quite obviously, such a pad can be used by itself outside of the combination disclosed herein with other colorimeters or spectrophotometers in which light may be reflected from a backup plate. It can also be used in combination with the pressure plate 64 in such other instruments to provide accurate and reproducible readings.

The above structure is preferably used in conjunction with the spectrophotometer disclosed in the aforementioned Application A and provides a basis for the calibration procedure disclosed therein. In other words, the invention provides a structure and mode of operation that can be readily calibrated to yield highly accurate and reproducible color measurements and analysis. While the head is constructed to minimize receiving specular components by bundles 54, nevertheless some specular reflectance is received but it can be readily compensated for by the calibration method. Additionally, it should be obvious that the illuminating light may be either variable monochromatic light or polychromatic light in which the reflected light can be analyzed through the use of a conventional monochromator.

It has been found that the reflectance of the sample is affected by the degree of pressure. If reflectance is measured versus pressure, the reflectance increases as pressure increases from 0 psi until a pressure is reached beyond which there is no appreciable change in the reflectance. Thus, the force exerted by spring 38 should be adjusted to provide a pressure on the sample within the range where reflectance does not vary with pressure. A suitable preferable pressure operating point is 4.7 ± .2 psi although pressures as low as 3 psi may be used. Below 3 psi, the reflectance varies with pressure too much. The pressure is believed to compress the textile fibers until they become dense enough to exhibit a stable or constant reflectance value.

It should be obvious that changes can be made by way of addition and omission to the details and arrangement of parts without departing from the spirit and scope of the invention as defined in the appended claims.

What is claimed is:
1. In apparatus for analyzing the color of a textile sample, the combination comprising:
 a housing of opaque material having a flat side, a cylindrical chamber therein opening through said flat side, a first cylindrical bore intercepting said chamber at a point opposite to said opening and extending substantially perpendicular to said opening, and a plurality of second cylindrical bores intersecting said chamber along the walls thereof, said second bores having axes that converge substantially to a point coincident with an extension to the axis of said first bore, the walls of said chamber and said first and second bores being blackened to minimize reflectance therefrom;
 a first fiber optic bundle having one end mounted in said first bore, the other end being operative to receive light for directly illuminating a test sample positioned against said housing at said opening;
 a plurality of second fiber optic bundles each having one end mounted in a different one of said second bores for receiving primarily diffuse light reflected from said sample, said ends of said second bundles being recessed in said second bores and located relative to said opening so that the only direct specular rays received by such ends are rays that have been reflected at least twice from said housing;
 a transparent glass plate mounted in said housing and covering said opening and providing a reference surface located a fixed distance from said ends of said fiber optic bundles;
 and support means adapted to press said test sample against said glass plate with a pressure in a range wherein the
 reflectance of said sample remains substantially constant with limited changes in pressure.

2. The combination of claim 1, wherein the ends of each of said second fiber optic bundles mounted in said second bores comprises fibers arranged in a rectangle extending across such bores.

3. The combination of claim 2 wherein:
 said first fiber optic bundle projects light substantially perpendicularly to said glass plate,
 and said second fiber optic bundles are arranged at substantially 45° relative to said plate.

4. The combination of claim 1, comprising:
 means mounting said housing and said support means for relative movement allowing said test sample to be removed and replaced by another item to be measured.

5. The combination of claim 4 comprising:
 adjustable means for setting said pressure to a predetermined operating point in said range.

* * * * *